US008530625B2

(12) United States Patent
Kaplan et al.

(10) Patent No.: US 8,530,625 B2
(45) Date of Patent: *Sep. 10, 2013

(54) SILK-BASED DRUG DELIVERY SYSTEM

(75) Inventors: David L. Kaplan, Concord, MA (US); Lorenz Meinel, Kassel (DE)

(73) Assignees: Trustees of Tufts College, Medford, MA (US); Eidgenossisches Technische Hochschule (The Swiss Federal Institute of Technology), Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,264

(22) Filed: Apr. 10, 2012

(65) Prior Publication Data

US 2012/0195967 A1    Aug. 2, 2012

Related U.S. Application Data

(63) Continuation of application No. 11/628,930, filed as application No. PCT/US2005/020844 on Jun. 13, 2005, now Pat. No. 8,178,656.

(60) Provisional application No. 60/579,065, filed on Jun. 11, 2004.

(51) Int. Cl.
*A61K 38/17* (2006.01)
*A61K 9/22* (2006.01)

(52) U.S. Cl.
USPC .......................................... 530/353; 424/468

(58) Field of Classification Search
None
See application file for complete search history.

(56) References Cited

U.S. PATENT DOCUMENTS 7,057,023 B2 *   6/2006   Islam et al. ................... 530/412

OTHER PUBLICATIONS

Kweon, H., et al. 2001 Journal of Applied Polymer Science 80: 928-934.*
Nazarov, R., et al. 2004 Biomacromolecules 5: 718-726.*
Serizawa, T., et al. 2002 Macromolecules 35: 8656-8658.*
Pettit, D.K., et al. 1998 Tibtech 16: 343-349.*
Hanawa, et al., "New Oral Dosage Form Elderly Patients. III. Stability of Trichlormethiazide in Silk Fibroin Gel and Various Sugar Solutions" vol. 26 No. 10, pp. 1091-1097, 2000, Drug Development and Industrial Pharmacy.
Hanawa et al., "New Oral Dosage Form for Elderly Patients. II. Release Behavior of Benfotiamine from Silk Fibroin Gel", vol. 43 No. 5, pp. 872-876, 1995, Chem. Pharm. Bull.
Hanaway et al., "New Oral Dosage Form for Elderly Patients: Preparation and Characterization of Silk Fibroin Gel", vol. 43 No. 2, pp. 284-288, 1995, Chem. Pharm. Bull.
Altman et al., "Silk-based Biomaterials", vol. 24, pp. 401-416, 2003, Biomaterials.
Kim, et al., "Structure and Properties of Silk Hydrogels" vol. 5 No. 3, pp. 786-792, 2004, Biomacromolecules.
Yao et al., "Synthesis and Structural Characterization of Silk-Like Materials Incorporated with an Elastic Motif", vol. 133 No. 1, pp. 147-154, 2003, J. Biochemistry.
Tsukada, et al., "Preparation and Application of Porous Silk Fibroin Materials" vol. 54, pp. 517-214, 1994, Journal of Applied Polymer Science.
Cappello et al., "In-situ Self-assembling Protein Polymer Gel Systems for Administration, Delivery, and Release of Drugs" vol. 53, pp. 105-117, 1998, Journal of Controlled Release.

* cited by examiner

*Primary Examiner* — Marsha Tsay
(74) *Attorney, Agent, or Firm* — Nixon Peabody LLP

(57) ABSTRACT

The present invention provides for novel sustained release silk-based delivery systems. The invention further provides methods for producing such formulations. In general, a silk fibroin solution is combined with a therapeutic agent to form a silk fibroin article. The article is then treated in such a way as to alter its conformation. The change in conformation increases its crytallinity or liquid crystallinity, thus controlling the release of a therapeutic agent from the formulation. This can be accomplished as single material carriers or in a layer-by-layer fashion to load different therapeutic agents or different concentrations of these agents in each layer.

16 Claims, 10 Drawing Sheets

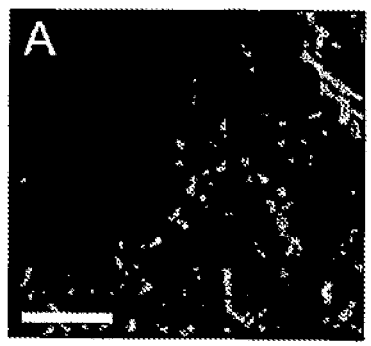
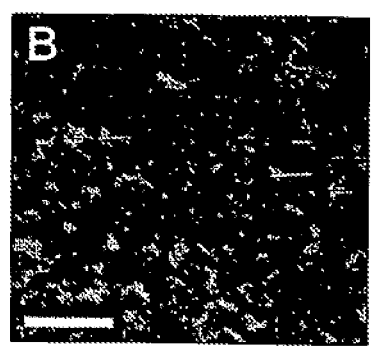
FIG. 6A  FIG. 6B
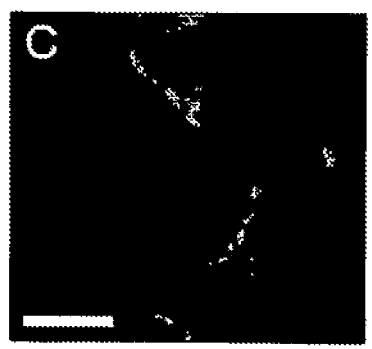
FIG. 6C  FIG. 6D

SILK-BASED DRUG DELIVERY SYSTEM

CROSS REFERENCE TO RELATED APPLICATIONS

This application is a continuation under 35 U.S.C. 120, 121, or 365(c) of U.S. patent application Ser. No. 11/628,930 filed Oct. 23, 2007 which is a 371 National Stage Entry of International Application No. PCT/US2005/020844 filed on Jun. 13, 2005, which designated the U.S., and which claims the benefit under 35 U.S.C. §119(e) of U.S. Provisional Application No. 60/579,065 filed on Jun. 11, 2004. The contents of each of these applications is hereby incorporated by reference in its entirety.

GOVERNMENT SUPPORT

This invention was supported by the NIH and the government of the United States has certain rights thereto.

FIELD OF THE INVENTION

The present invention relates generally to a silk-based drug delivery system. In particular, the system is capable of releasing a therapeutic agent from the device at a sustained and controllable rate.

BACKGROUND OF THE INVENTION

Silk, as the term is generally known in the art, means a filamentous fiber product secreted by an organism such as a silkworm or spider. Silks produced from insects, namely (i) *Bombyx mori* silkworms, and (ii) the glands of spiders, typically *Nephilia clavipes*, are the most often studied forms of the material; however, hundreds to thousands of natural variants of silk exist in nature. Fibroin is produced and secreted by a silkworm's two silk glands.

Silkworm silk has been used in biomedical applications for over 1,000 years. The *Bombyx mori* specie of silkworm produces a silk fiber (known as a "bave") and uses the fiber to build its cocoon. The bave, as produced, includes two fibroin filaments or "broins", which are surrounded with a coating of gum, known as sericin—the silk fibroin filament possesses significant mechanical integrity. When silk fibers are harvested for producing yarns or textiles, including sutures, a plurality of fibers can be aligned together, and the sericin is partially dissolved and then resolidified to create a larger silk fiber structure having more than two broins mutually embedded in a sericin coating.

The unique mechanical properties of reprocessed silk such as fibroin and its biocompatibility make the silk fibers especially attractive for use in biotechnological materials and medical applications. Silk provides an important set of material options for biomaterials and tissue engineering because of the impressive mechanical properties, biocompatibility and biodegradability (Altman, G. H., et al., Biomaterials 2003, 24, 401-416; Cappello, J., et al., J. Control. Release 1998, 53, 105-117; Foo, C. W. P., et al., Adv. Drug Deliver. Rev. 2002, 54, 1131-1143; Dinerman, A. A., et al., J. Control. Release 2002, 82, 277-287; Megeed, Z., et al., Adv. Drug Deliver. Rev. 2002, 54, 1075-1091; Petrini, P., et al., J. Mater. Sci-Mater. M. 2001, 12, 849-853; Altman, G. H., et al., Biomaterials 2002, 23, 4131-4141; Panilaitis, B., et al., Biomaterials 2003, 24, 3079-3085). For example, 3-dimensional porous silk scaffolds have been described for use in tissue engineering (Meinel et al., Ann Biomed Eng. 2004 January; 32(1):112-22; Nazarov, R., et al., Biomacromolecules in press). Further, regenerated silk fibroin films have been explored as oxygen- and drug-permeable membranes, supports for enzyme immobilization, and substrates for cell culture (Minoura, N., et al., Polymer 1990, 31, 265-269; Chen, J., et al., Minoura, N., Tanioka, A. 1994, 35, 2853-2856; Tsukada, M., et al., Polym. Sci. Part B Polym. Physics 1994, 32, 961-968).

The desirability of sustained release has long been recognized in the pharmaceutical field. Sustained-release drug-delivery systems can provide many benefits over conventional dosage forms. Generally, sustained-release preparations provide a longer period of therapeutic or prophylactic response compared to conventional rapid release dosage forms. For example, in treatment of pain, sustained-release formulations are useful to maintain relatively constant analgesic drug release rates over a period of time, for example 12-24 hours, so that blood serum concentration of the drug remains at a therapeutically effective level for a longer duration than is possible with a conventional dosage form of the drug. In addition, whereas standard dosage forms typically exhibit high initial drug release rates that can result in unnecessarily elevated blood serum levels of the drug, sustained-release formulations can help maintain blood serum levels of the drug at or slightly above the therapeutically effective threshold. Such reduced fluctuation in blood serum concentration of the drug can also help prevent excess dosing.

Furthermore, sustained-release compositions, by optimizing the kinetics of delivery, also increase patient compliance as patients are less likely to miss a dose with less frequent administration, particularly when a once-a-day dosage regimen is possible; less frequent administration also increases patient convenience. Sustained-release formulations may also reduce overall healthcare costs. Although the initial cost of sustained-release delivery systems may be greater than the costs associated with conventional delivery systems, average costs of extended treatment over time can be lower due to less frequent dosing, enhanced therapeutic benefit, reduced side-effects, and a reduction in the time required to dispense and administer the drug and monitor patient compliance.

Many polymer-based systems have been proposed to accomplish the goal of sustained release. These systems generally have relied upon either degradation of the polymer or diffusion through the polymer as a means to control release.

Polymer-based attempts to develop sustained-release formulations have included the use of a variety of biodegradable and non-biodegradable polymer (e.g. poly(lactide-co-glycolide)) microparticles containing the active ingredient (see e.g., Wise et al., Contracgption, 1:227-234 (1973); and Hutchinson et al., Biochem. Soc. Trans., 13:520-523 (1985)), and a variety of techniques are known by which active agents, e.g. proteins, can be incorporated into polymeric microspheres (see e.g., U.S. Pat. No. 4,675,189 and references cited therein). In addition, various microcapsules, microparticles, and larger sustained-release implants have been used to deliver pharmaceuticals to patients over an extended period of time. For example, polyesters such as poly-DL-lactic acid, polyglycolic acid, polylactide, and other copolymers, have been used to release biologically active molecules such as progesterone and luteinizing hormone-releasing hormone (LH-RH) analogs, e.g., as described in Kent et al., U.S. Pat. No. 4,675,189, and Hutchinson et al., U.S. Pat. No. 4,767,628.

Unfortunately, the successes of current polymer-based sustained delivery systems have been limited. This is due, in large part, to their necessity on using organic solvents during preparation. Even solvents which are well tolerated in vivo, i.e. ethylacetate, may cause immunological reactions or anaphylactic shock. In addition, all organic solvents are volatile and require expensive production processes.

There is, therefore, a need for a biocompatible, biodegradable, sustained-release drug-delivery system. Such products should have the desired mechanical properties of tensile strength, elasticity, formability, and the like, provide for controlled resorption, and be physiologically acceptable. Moreover, such products should allow for ease of administration for a variety of in vivo indications and in best-case scenarios be inexpensive to manufacture.

SUMMARY OF THE INVENTION

The present invention provides a novel sustained release silk-based drug delivery system. The invention further provides methods for producing such devices.

In one embodiment, a method for producing a pharmaceutical formulation for controlled release of a therapeutic agent is provided. The method comprises contacting a silk fibroin solution with the therapeutic agent. Therapeutic agents include, for example, proteins, peptides and small molecules. In a preferred embodiment, an aqueous silk fibroin solution is utilized.

Next, a silk fibroin article that contains the therapeutic agent is formed. The silk fibroin article may be a thread, fiber, film, foam, mesh, hydrogel, three-dimensional scaffold, tablet filling material, tablet coating, or microsphere.

The conformation of the article is then altered in order to increase its crystallinity or liquid crystallinity, thus providing controlled release of the therapeutic agent from the silk fibroin article.

In one embodiment of the present invention, the conformation of the article is altered by contacting the fibroin article with methanol. The methanol concentration is at least 50%, at least 70%, at least 90% or at least 100%.

In an alternative embodiment, alteration in the conformation of the fibroin article is induced by treating the article with sheer stress. The sheer stress may be applied by passing the article through a needle.

The conformation of the fibroin article may also be altered by contacting the article with an electric field, by applying pressure, or by contacting the article with salt.

Preferably, the therapeutic agent is equal to or greater than about 10 kilodaltons (kDa). More preferably the therapeutic agent is greater than about 20 kDa.

In a further embodiment, a pharmaceutical formulation with a plurality of silk fibroin articles (i.e. layers) is provided. In this embodiment, at least one layer has an induced conformational change that differs from at least one other layer. The silk fibroin article layers may each contain different therapeutic agents, each layer having the same or different induced conformational changes.

The pharmaceutical formulation is biodegradable and may comprise a targeting agent that specifically targets the device to a specific cell or tissue type. The targeting agent may be, for example, a sugar, peptide, or fatty acid.

In one embodiment, the silk fibroin solution is obtained from a solution containing a dissolved silkworm silk, such as, for example, from *Bombyx mori*. Alternatively, the silk fibroin solution is obtained from a solution containing a dissolved spider silk, such as, for example, from *Nephila clavipes*. The silk fibroin solution may also be obtained from a solution containing a genetically engineered silk. In one embodiment, the genetically engineered silk comprises a therapeutic agent. This may be a fusion protein with a cytokine, an enzyme, or any number of hormones or peptide-based drugs, antimicrobials and related substrates.

Also encompassed in the present invention is the pharmaceutical formulation for controlled release of a therapeutic agent, produced by the above methods.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIG. 6 shows AFM images of native silk films (6A, 6C) or films treated with methanol (6B, 6D). Bar length 2.5 µm (6A, 6B) and 0.5 µm (6B, 6D).

DETAILED DESCRIPTION OF THE INVENTION

Figure 1:
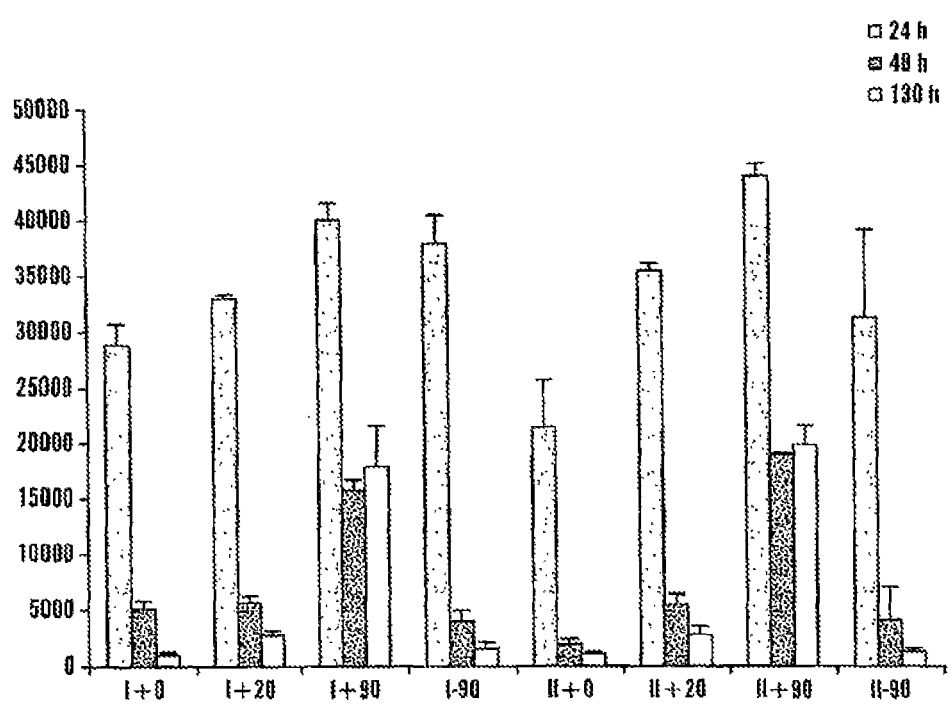
FIG. 1 shows the drug release of FD4 after 24, 48, and 130 hours.

Methods for preparation of silk-based drug delivery systems are described. In particular, the drug delivery system allows for the controlled and sustained release of therapeutic agents in vivo. In general, a silk fibroin solution is combined with a therapeutic agent to form a silk fibroin article. The article is then treated in such a way as to alter its conformation. The change in conformation increases its crystallinity, thus controlling the release of a therapeutic agent from the formulation.

As used herein, the term "fibroin" includes silkworm fibroin and insect or spider silk protein (Lucas et al., *Adv. Protein Chem* 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavipes*. In the alternative, the silk proteins suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The silk fibroin solution can be prepared by any conventional method known to one skilled in the art. For example, *B. mori* cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. Preferably, the extracted silk is dissolved in about 9-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin.

Preferably, the PEG is of a molecular weight of 8,000-10,000 g/mol and has a concentration of 25-50%. A slide-a-lyzer dialysis cassette (Pierce, MW CO 3500) is preferably used. However, any dialysis system may be used. The dialysis is for a time period sufficient to result in a final concentration of aqueous silk solution between 10-30%. In most cases dialysis for 2-12 hours is sufficient. See, for example, PCT application PCT/US/04/11199.

Alternatively, the silk fibroin solution can be produced using organic solvents. Such methods have been described, for example, in Li, M., et al., J. Appl. Poly Sci. 2001, 79, 2192-2199; Min, S., et al. Sen'I Gakkaishi 1997, 54, 85-92; Nazarov, R. et al., Biomacromolecules 2004 May-June; 5(3): 718-26.

In accordance with the present invention, the silk fibroin solutions contain at least one therapeutic agent. The silk fibroin solution is contacted with a therapeutic agent prior to forming the fibroin article, e.g. a fiber, mesh, scaffold, or loaded into the article after it is formed. For loading after formation, silk assembly is used to control hydrophilic/hydrophobic partitioning (see, for example, Jin et al., Nature. 2003 Aug. 28; 424(6952):1057-61) and the adsorption of phase separation of the therapeutic agent. The material can also be loaded by entrapping the therapeutic agent in the silk by inducing the transition to the beta sheet (e.g. methanol, shear, salts, electric) and adding layers on this with each layer entrapping the next therapeutic. This layer-by-layer approach would allow onion like structures with selective loading in each layer.

The variety of different therapeutic agents that can be used in conjunction with the formulations of the present invention is vast and includes small molecules, proteins, peptides and nucleic acids. In general, therapeutic agents which may be administered via the invention include, without limitation: anti-infectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); anti-angiogenic proteins such as endostatin, and other naturally derived or genetically engineered proteins, polysaccharides, glycoproteins, or lipoproteins. Growth factors are described in The Cellular and Molecular Basis of Bone Formation and Repair by Vicki Rosen and R. Scott Thies, published by R. G. Landes Company, hereby incorporated herein by reference.

Additionally, the silk based devices of the present invention can be used to deliver any type of molecular compound, such as, pharmacological materials, vitamins, sedatives, steroids, hypnotics, antibiotics, chemotherapeutic agents, prostaglandins, and radiopharmaceuticals. The delivery system of the present invention is suitable for delivery of the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

Additionally, the pharmaceutical formulation of the present invention may also have a targeting ligand. Targeting ligand refers to any material or substance which may promote targeting of the pharmaceutical formulation to tissues and/or receptors in vivo and/or in vitro with the formulations of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin. The pharmaceutical formulations of the present invention may also encompass precursor targeting ligands. A precursor to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and [agr]-iodo acetyl groups.

Silk formulations containing bioactive materials may be formulated by mixing one or more therapeutic agents with the silk solution used to make the article. Alternatively, a therapeutic agent can be coated onto the pre-formed silk fibroin article, preferably with a pharmaceutically acceptable carrier. Any pharmaceutical carrier can be used that does not dissolve the silk material. The therapeutic agents may be present as a liquid, a finely divided solid, or any other appropriate physical form.

The above described silk fibroin solution, which contains at least one therapeutic agent, is next processed into a thread, fiber, film, mesh, hydrogel, three-dimensional scaffold, tablet filling material, tablet coating, or microsphere. Methods for generating such are well known in the art. See, e.g. Altman, et al., Biomaterials 24:401, 2003; PCT Publications, WO 2004/000915 and WO 2004/001103; and PCT Application No's PCT/US/04/11199 and PCT/US04/00255, which are herein incorporated by reference.

Silk films can be produced by preparing the concentrated aqueous silk fibroin solution and casting the solution. See, for example PCT application PCT/US/04/11199. The film can be contacted with water or water vapor, in the absence of alcohol. The film can then be drawn or stretched mono-axially or biaxially. The stretching of a silk blend film induces molecular alignment of the film and thereby improves the mechanical properties of the film.

If desired, the film comprises from about 50 to about 99.99 part by volume aqueous silk protein solution and from about 0.01 to about 50 part by volume biocompatible polymer e.g., polyethylene oxide (PEO). Preferably, the resulting silk blend film is from about 60 to about 240 μm thick, however, thicker samples can easily be formed by using larger volumes or by depositing multiple layers.

Foams may be made from methods known in the art, including, for example, freeze—drying and gas foaming in which water is the solvent or nitrogen or other gas is the blowing agent, respectively. Alternately, the foam is made by contacting the silk fibroin solution with granular salt. The pore size of foams can be controlled, for example by adjusting the concentration of silk fibroin and the particle size of a granular salt (for example, the preferred diameter of the salt particle is between about 50 microns and about 1000 microns). The salts can be monovalent or divalent. Preferred salts are monovalent, such as NaCl and KCl. Divalent salts, such as CaCl2 can also be used. Contacting the concentrated silk fibroin solution with salt is sufficient to induce a conformational change of the amorphous silk to a □-sheet structure that is insoluble in the solution. After formation of the foam, the excess salt is then extracted, for example, by immersing in water. The resultant porous foam can then be dried and the foam can be used, for example, as a cell scaffold in biomedical application. See, for example PCT application PCT/US/04/11199.

In one embodiment, the foam is micropatterned foam. Micropatterned foams can be prepared using, for example, the method set forth in U.S. Pat. No. 6,423,252, the disclosure of which is incorporated herein by reference. The method comprises contacting the concentrated silk solution with a surface of a mold, the mold comprising on at least one surface thereof a three-dimensional negative configuration of a predetermined micropattern to be disposed on and integral with at least one surface of the foam, lyophilizing the solution while in contact with the micropatterned surface of the mold, thereby providing a lyophilized, micropatterned foam, and removing the lyophilized, micropatterned foam from the mold. Foams prepared according to this method comprise a predetermined and designed micropattern on at least one surface, which pattern is effective to facilitate tissue repair, ingrowth or regeneration.

Fibers may be produced using, for example, wet spinning or electrospinning. Alternatively, as the concentrated solution has a gel-like consistency, a fiber can be pulled directly from the solution.

Electrospinning can be performed by any means known in the art (see, for example, U.S. Pat. No. 6,110,590). Preferably, a steel capillary tube with a 1.0 mm internal diameter tip is mounted on an adjustable, electrically insulated stand. Preferably, the capillary tube is maintained at a high electric potential and mounted in the parallel plate geometry. The capillary tube is preferably connected to a syringe filled with silk solution. Preferably, a constant volume flow rate is maintained using a syringe pump, set to keep the solution at the tip of the tube without dripping. The electric potential, solution flow rate, and the distance between the capillary tip and the collection screen are adjusted so that a stable jet is obtained. Dry or wet fibers are collected by varying the distance between the capillary tip and the collection screen.

A collection screen suitable for collecting silk fibers can be a wire mesh, a polymeric mesh, or a water bath. Alternatively and preferably, the collection screen is an aluminum foil. The aluminum foil can be coated with Teflon fluid to make peeling off the silk fibers easier. One skilled in the art will be able to readily select other means of collecting the fiber solution as it travels through the electric field. The electric potential difference between the capillary tip and the aluminum foil counter electrode is, preferably, gradually increased to about 12 kV, however, one skilled in the art should be able to adjust the electric potential to achieve suitable jet stream.

The present invention additionally provides a non-woven network of fibers comprising a pharmaceutical formulation of the present invention. The fiber may also be formed into yarns and fabrics including for example, woven or weaved fabrics.

The fibroin silk article of the present invention may also be coated onto various shaped articles including biomedical devices (e.g. stents), and silk or other fibers, including fragments of such fibers.

Silk hydrogels can be prepared by methods known in the art, see for example PCT application PCT/US/04/11199. The sol-gel transition of the concentrated silk fibroin solution can be modified by changes in silk fibroin concentration, temperature, salt concentrations (e.g. CaCl2, NaCl, and KCl), pH, hydrophilic polymers, and the like. Before the sol-gel transition, the concentrated aqueous silk solution can be placed in a mold or form. The resulting hydrogel can then be cut into any shape, using, for example a laser.

The silk fibroin articles described herein can be further modified after fabrication. For example, the scaffolds can be coated with additives, such as bioactive substances that function as receptors or chemoattractors for a desired population of cells. The coating can be applied through absorption or chemical bonding.

Additives suitable for use with the present invention include biologically or pharmaceutically active compounds. Examples of biologically active compounds include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials. November; 24(24):4385-415); biologically active ligands; and substances that enhance or exclude particular varieties of cellular or tissue ingrowth. Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-□ and the like. As used herein, the term additive also encompasses antibodies, DNA, RNA, modified RNA/protein composites, glycogens or other sugars, and alcohols.

Biocompatible polymers can be added to the silk article to generate composite matrices in the process of the present invention.

Biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). Two or more biocompatible polymers can be used.

As a next step in the method for producing pharmaceutical formulations for controlled release of therapeutic agents, the conformation of the silk fibroin article is altered. The induced conformational change alters the crystallinity of the article, thus altering the rate of release of the therapeutic agent from the silk fibroin article. The conformational change may be induced by treating the fibroin article with methanol. The methanol concentration is at least 50%, at least 70%, at least 90% or at least 100%.

Alternatively, the alteration in the conformation of the fibroin article may be induced by treating the article with sheer stress. The sheer stress may be applied, for example, by passing the article through a needle. Other methods of inducing conformational changes include contacting the article with an electric field, salt or by applying pressure.

The silk-based drug delivery system of the present invention may comprise a plurality (i.e. layers) of silk fibroin articles, where at least one silk fibroin article may have an induced conformational change that differs from at least one alternative silk fibroin article. For example, each layer may have different solutions of fibroin (concentrations, drugs) and have different conformational changes. These can be combined in various sequences to create 'onion-like' structures such that the delivery vehicle will offer changing rates of release of each layer depending on crystallinity, thickness, concentration of drug, type of drug, etc. This approach is very amenable to scale up and combinatorial or related approaches to formulation to create multiple control points in release profiles and drug combinations.

Figure 3:
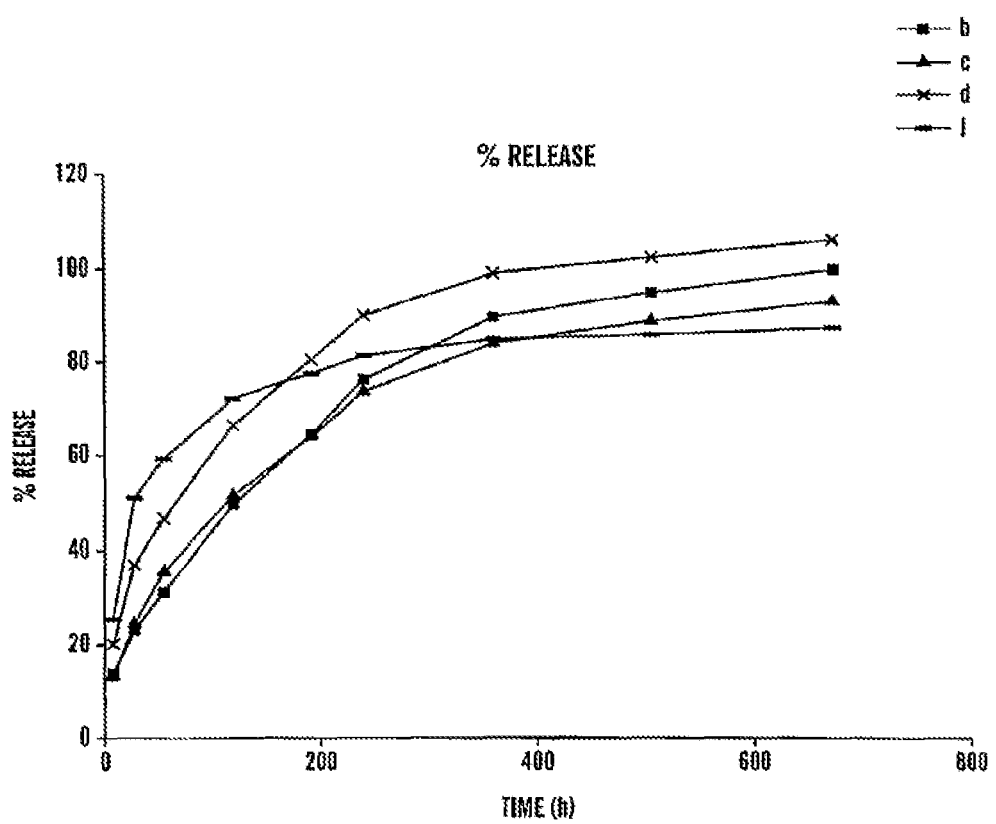
FIG. 3 shows coating of core with silk fibroin solution treated with different concentrations of methanol (I) core without coating; (d) core with coating treated with 90% methanol solution; (c) core with two layers of fibroin; and (b) core with three layers of fibroin. The results demonstrate that the release of a therapeutic can be controlled through the thickness of the coating around the core.

Additionally, the release of the therapeutic agent from the pharmaceutical formulations of the present invention can be controlled through the thickness of the silk fibroin article. As shown in FIG. 3, with increasing article thickness, the initial burst and amount of drug released within the first 100 hours was reduced. However, the sustained release of drug over time was significantly higher with increasing film numbers.

Drug delivery composites are also encompassed. A family of such structures are prepared as above and then dispersed in various amounts into the fibroin hydrogels. These composite systems would then be used in various modes of delivery, such as, for example, the "onion-like" vehicles described above.

The materials produced using the present invention, e.g., hydrogels, fibers, films, foams, or meshes, may be used in a variety of medical applications such as a drug (e.g, small molecule, protein, or nucleic acid) delivery device, including controlled release systems.

Controlled release permits dosages to be administered over time, with controlled release kinetics. In some instances, delivery of the therapeutic agent is continuous to the site where treatment is needed, for example, over several weeks. Controlled release over time, for example, over several days or weeks, or longer, permits continuous delivery of the therapeutic agent to obtain optimal treatment. The controlled delivery vehicle is advantageous because it protects the therapeutic agent from degradation in vivo in body fluids and tissue, for example, by proteases.

Controlled release from the pharmaceutical formulation may be designed to occur over time, for example, for greater than about 12 or 24 hours. The time of release may be selected, for example, to occur over a time period of about 12 hours to 24 hours; about 12 hours to 42 hours; or, e.g., about 12 to 72 hours. In another embodiment, release may occur for example on the order of about 2 to 90 days, for example, about 3 to 60 days. In one embodiment, the therapeutic agent is delivered locally over a time period of about 7-21 days, or about 3 to 10 days. In other instances, the therapeutic agent is administered over 1, 2, 3 or more weeks in a controlled dosage. The controlled release time may be selected based on the condition treated. For example, longer times may be more effective for wound healing, whereas shorter delivery times may be more useful for some cardiovascular applications.

Controlled release of the therapeutic agent from the fibroin article in vivo may occur, for example, in the amount of about 1 ng to 1 mg/day, for example, about 50 ng to 500 pg/day, or, in one embodiment, about 100 ng/day. Delivery systems comprising therapeutic agent and a carrier may be formulated that include, for example, 10 ng to 1 mg therapeutic agent, or in another embodiment, about 1 ug to 500 ug, or, for example, about 10 ug to 100 ug, depending on the therapeutic application.

The silk-based drug delivery vehicle may be administered by a variety of routes known in the art including topical, oral, parenteral (including intravenous, intraperitoneal, intramuscular and subcutaneous injection as well as intranasal or inhalation administration) and implantation. The delivery may be systemic, regional, or local. Additionally, the delivery may be intrathecal, e.g., for CNS delivery. For example, administration of the pharmaceutical formulation for the treatment of wounds may be by topical application, systemic administration by enteral or parenteral routes, or local or regional injection or implantation. The silk-based vehicle may be formulated into appropriate forms for different routes of administration as described in the art, for example, in "Remington: The Science and Practice of Pharmacy", Mack Publishing Company, Pennsylvania, 1995, the disclosure of which is incorporated herein by reference.

The controlled release vehicle may include excipients available in the art, such as diluents, solvents, buffers, solubilizers, suspending agents, viscosity controlling agents, binders, lubricants, surfactants, preservatives and stabilizers. The formulations may include bulking agents, chelating agents, and antioxidants. Where parenteral formulations are used, the formulation may additionally or alternately include sugars, amino acids, or electrolytes.

Excipients include polyols, for example of a molecular weight less than about 70,000 kD, such as trehalose, mannitol, and polyethylene glycol. See for example, U.S. Pat. No. 5,589,167, the disclosure of which is incorporated herein. Exemplary surfactants include nonionic surfactants, such as Tweeng surfactants, polysorbates, such as polysorbate 20 or 80, etc., and the poloxamers, such as poloxamer 184 or 188, Pluronic (r) polyols, and other ethylene/polypropylene block polymers, etc. Buffers include Tris, citrate, succinate, acetate, or histidine buffers. Preservatives include phenol, benzyl alcohol, metacresol, methyl paraben, propyl paraben, benzalconium chloride, and benzethonium chloride. Other additives include carboxymethylcellulose, dextran, and gelatin. Stabilizing agents include heparin, pentosan polysulfate and other heparinoids, and divalent cations such as magnesium and zinc.

The pharmaceutical formulation of the present invention may be sterilized using conventional sterilization process such as radiation based sterilization (i.e. gamma-ray), chemical based sterilization (ethylene oxide), autoclaving, or other appropriate procedures. Preferably the sterilization process will be with ethylene oxide at a temperature between 52-55° C. for a time of 8 or less hours. After sterilization the formulation may be packaged in an appropriate sterilize moisture resistant package for shipment.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

The invention will be further characterized by the following examples which are intended to be exemplary of the invention.

EXAMPLES

Example I

Materials and Methods: Preparation of Silk

Silk cocoons were cut in quarters and washed in $Na_2CO_3$ solution for 1 hour. The silk was washed 2 times with hot water and 20 times with cold water. Silk was dried over night and dissolved in 9M LiBr to become a 10% silk-fibroin solution. The solution was centrifuged at 27,000 g for 30 minutes and the supernatant was transferred in a dialysis cassette (MWCO 3,500) and dialyzed for 2 days. Silk-fibroin concentration was adjusted to 5% (m/V in water) by evaporation at 250 mbar and 45° C. The resulting silk solution was either mixed with a solution of FITC coupled to dextran (molecular weight of 4 kDa; FD4; concentration 10 mg/ml, Sigma) in a ratio of 150 ul silk-fibroin solution to 20 ul of FD4 solution, or the FD-4 was added later for control groups (see table 1). As a further group, parts of this solution were sonicated with 50 Hz, 2 A, 10 sec (Hielscher, UP200H). 170 ul of the solution (FD-4/silk mixture) was added into each well of a 96 well plate. For control, wells were filled with 150 ul of the silk-fibroin solution. Water was evaporated over night at room temperature and 250 mbar. 20 ul of the FD4 solution was added to the wells, which received the silk-fibroin solution only (to analyze the effect of mixing the drug with the solved silk-fibroin vs. later incubation of the solid films). Further wells were not incubated with silk (to analyze a possible fluorescence of the silk-fibroin films themselves). The films were either treated with water, methanol 20% or methanol 90% (V/V) for 3 hours. The solutions were aspirated and replaced by 300 ul PBS for the drug release study. Total release medium was replaced with fresh PBS after 24, 48, 130 hours and fluorescence was read with a Lumicounter (Packard, 480V, Gain Level, 1, ex. 485 nm, em. 530 nm).

Results & Discussion:

Plain silk-fibroin films do not show fluorescence. Without MeOH treatment or treatment with 20% MeOH, the release was characterized by a high initial burst and only minute release after 24 hours (Groups I+0 and I+20), although more FD4 was released when treated with 20% MeOH. This is probably due to the reduced solubility of FD4 in presence of MeOH. When treated with 90% MeOH, significantly more FD4 was released after 48 and after 130 hours, demonstrating the feasibility to get a sustained release from silk polymers by inducing a transformational change (I+90). Similar to the observation with the groups I+0 and I+20, the increase in MeOH concentration to 90% results in a higher encapsulation of total FD4. An incubation of the prepared film with FD4 for 3 hours (I–90) results in a high initial burst, similar to the I+0 and I+20. The absence of a substantial sustained release is probably due to a hindrance of drug diffusion in the (amorphous) silk-fibroin films. Therefore, conformational changes do not substantially affect FD4 absorbed to the surface of the films. Essentially the same results were obtained for the groups, which were also treated with ultrasonication. However, a treatment with ultrasonication does not have an influence on drug release as compared to the non sonicated group.

In conclusion, a sustained release of drugs (FD4) can be obtained with silk-fibroin polymers, when a conformational change is induced with 90% MeOH. Ultrasonication does not have an impact on drug release.

Example 2

We evaluated the feasibility to formulate drug delivery systems based on silk-fibroin. The experiments started from an aqueous fibroin-drug solution, followed by a slow evaporation of the water resulting in a solid fibroin film with suspended drug molecules. A conformational change of the fibroin was induced through methanol treatment, resulting in an increase of crystallinity. The degree of crystallinity governed the release of the drug.

Results & Discussion

Dextrans coupled to a fluorescent dye were chosen as a model drug. They allow a straightforward assessment of the influence of drug molecular weight on swelling gels. FD4—a term used in this summary describes FITC (F) coupled to a dextran (D) with a molecular weight of 4,000 g/mol. A first set of experiments compared FD4 release from fibroin gels treated with water and ascending methanol concentrations (FIG. 2).

Figure 2:
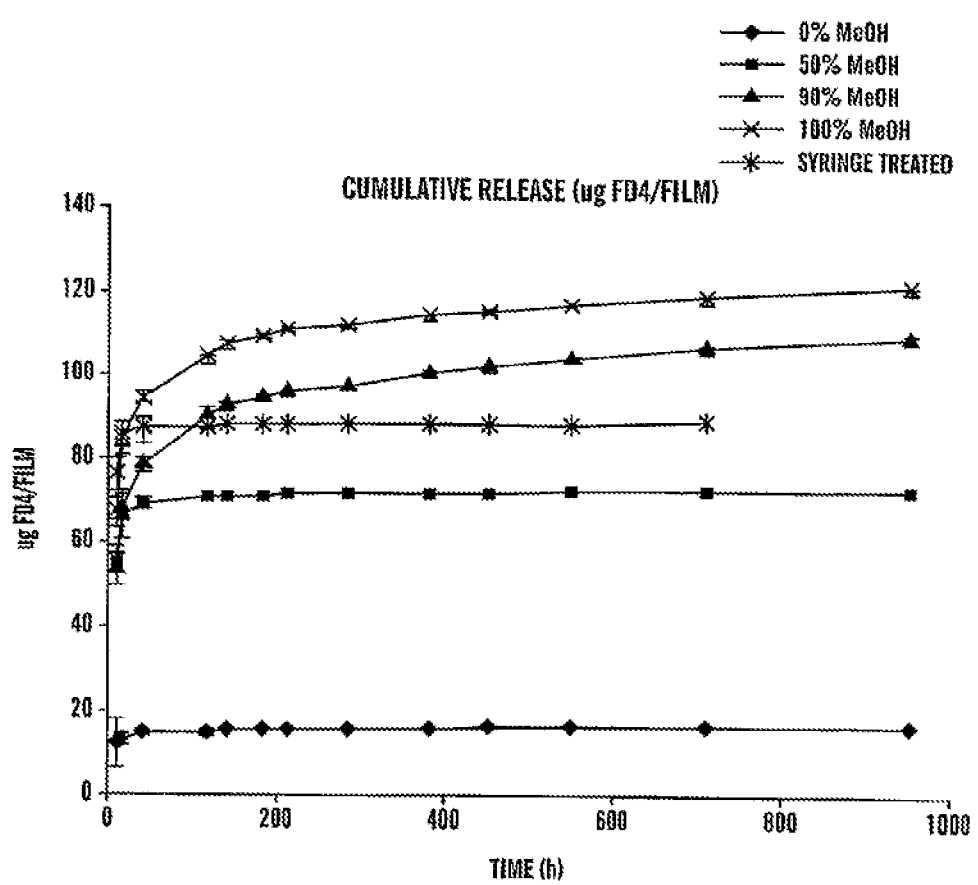
FIG. 2 shows the influence of methanol concentration on drug release. Treatment with methanol concentrations up to 50% results in a high burst release within the first 12 hours with minute amounts of FD4 released at later time points. In contrast, treatment with 90% or 100% methanol solutions results in a sustained and faster release for about 200 hours.

FIG. 2 shows the release of FD4 over time. The differences in maximum FD4 concentrations stems from different solubilities of the drug in methanol solutions of different concentrations or water. However, the release pattern was different. Treatment with methanol concentrations up to 50% resulted in a high burst release within the first 12 hours with minute amounts of FD4 released at later time points. In contrast, treatment with 90% or 100% methanol solutions resulted in a sustained and faster release for about 200 hours. At later time-points, the amount of drug released per time (slope) significantly decreased, with the release continuing throughout the observation period (exceeding 1,000 hours). Treatment with shear stress alone (syringe treated, FIG. 2) also induced gel formation through an increase of crystallinity.

To control the high initial burst—more than 30% of the total FD4 used—, identical films were prepared and treated with 90% methanol (core). This core was coated with additional layers of fibroin and again treated with 90% methanol solution or water (FIG. 3).

The results demonstrated in FIG. 3 show that the release can be controlled through the thickness of the coating around the core. With increasing film thickness (d-b-c in FIG. 3), the initial burst was reduced, the amount of drug released within the first 50 hours significantly less as compared to the core (I, FIG. 3), and the drug release (slope) was significantly higher for the coated cores than for the uncoated one. In particular the cores coated with 2 (c) or 3 (b) layers of fibroin had a nearly linear release for the first 300 hours (about 12.5 days), following zero order kinetics. The coating had a minimal effect on drug release, when treated with water instead of methanol solution, demonstrating the importance of inducing the conformational change (data not shown).

These findings allow for at least 2 conclusions: (i) silk fibroin when treated with methanol solution can be used to fabricate a controlled drug delivery system; and (ii) silk-fibroin coatings, treated with methanol solution can modify the release of drugs from a drug containing core.

This allows for numerous applications, including the preparation of microspheres or the coating of tablets to modify the release.

Example 3

Figure 7A:
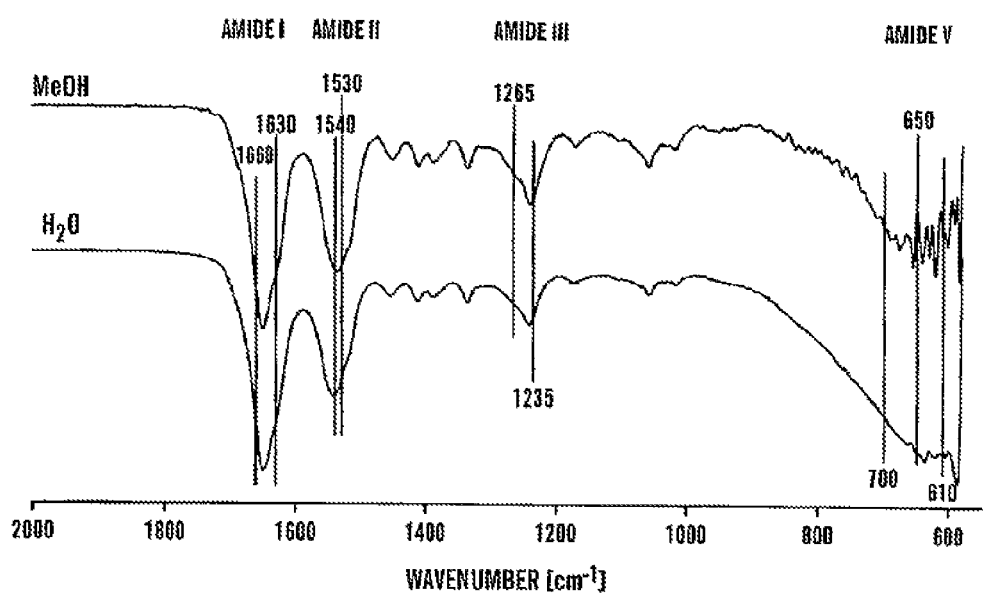
FIG. 7 shows physicochemical characterization of native silk films or films treated with methanol. (7A) FTIR analysis and X-ray diffractogram of methanol treated (7B) and untreated (7C) films. Contact angle measurements of a water drop on methanol treated (7D) and untreated (7E) films over time.

The exposure of silk films to methanol suggested an increase in crystallinity, as determined by FTIR analysis (FIG. 7A). This finding was based on a Amide II bond shift from 1540 cm$^{-1}$ to 1535 cm$^{-1}$, a finding typical for the increase in β-crystalline structures. Similarly, an additional shoulder appeared in response to methanol treatment at 1630 cm-1 (Amide I) and 1265 cm-1 (Amide III).

Figure 7B:
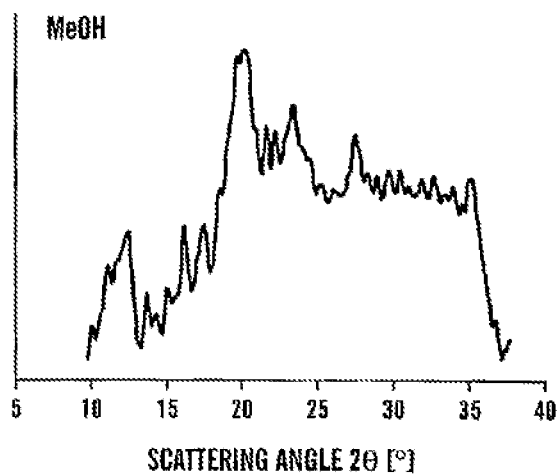
Figure 7C:
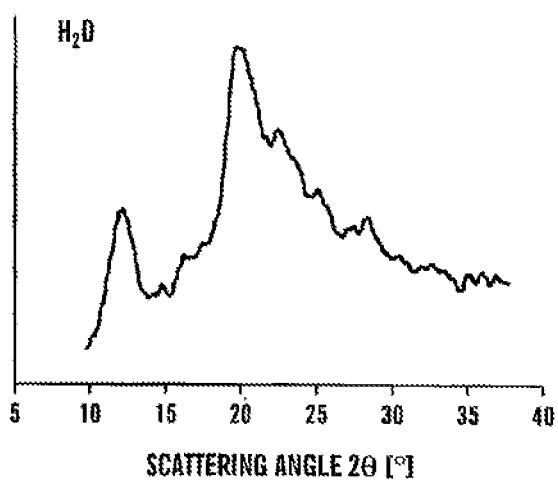
Figure 7D:
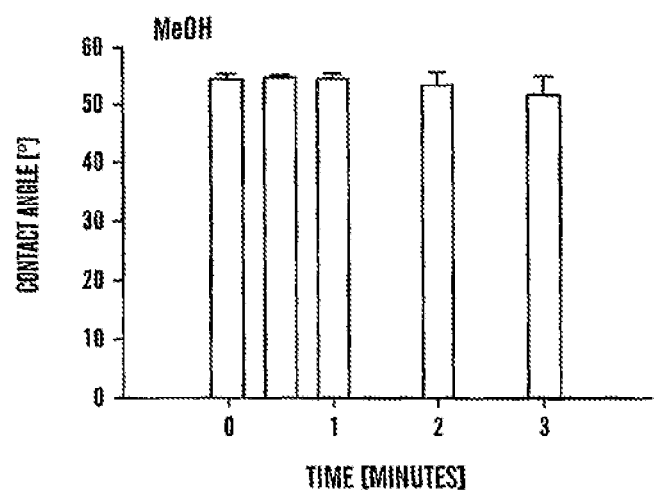
Figure 7E:
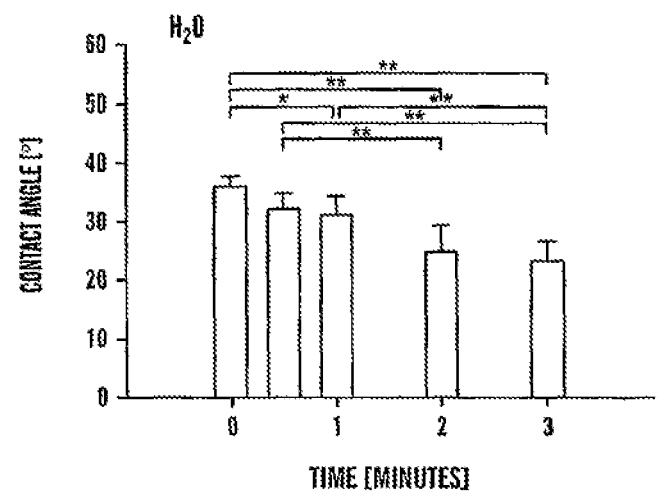

This data was corroborated by X-ray diffractometry (FIGS. 7B and 7C). The hydrophobicity of the film surfaces were significantly influenced by the crystallinity change of the films in response to methanol treatment, as determined by contact angle measurements (FIGS. 7D and 7E). For methanol treated films no change of the contact angle was observed over time, indicating the water-insolubility of these films as opposed to water treated films, in which a rapid decrease in contact angles resulted after 3 minutes of exposure to a water droplet.

Figure 5A:
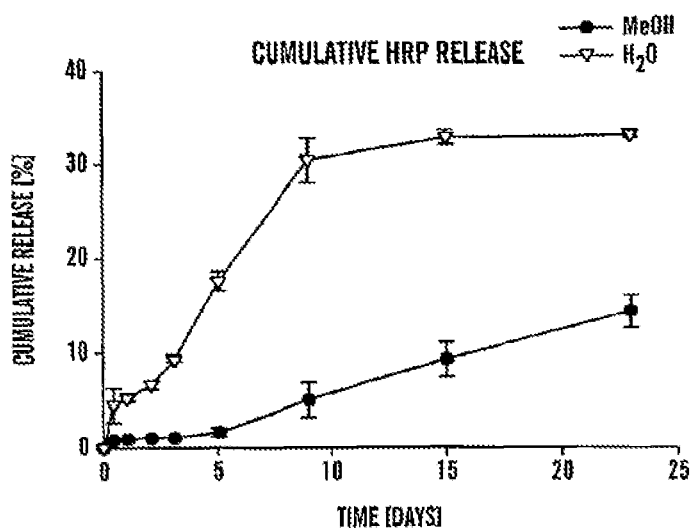
FIG. 5 shows cumulative release and adsorption of horseradish peroxidase (HRP; 5A, 5C) and Lysozyme (Lys, 5B, 5D) from silk films treated with methanol or H2O, respectively.
Figure 5B:
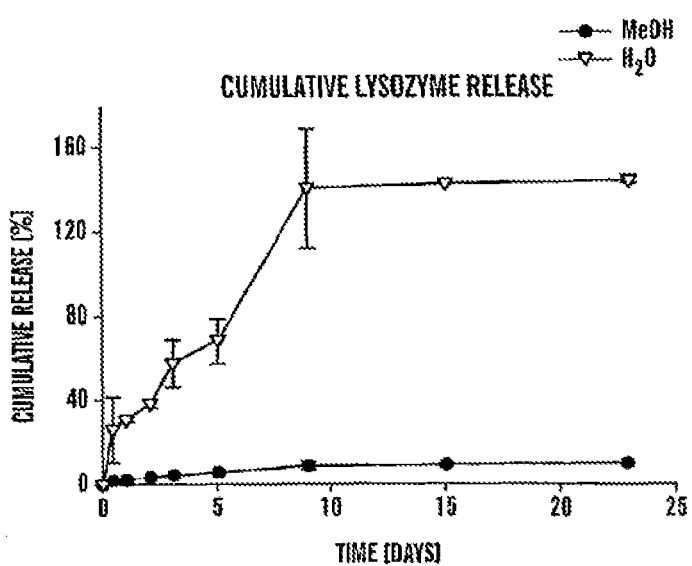

The topology of silk films before and after methanol treatment was assessed by atomic force microscopy (FIG. 6). Exposure to methanol as opposed to untreated films resulted in a rougher surface (FIGS. 6A and 6B) and the formation of globular structures (FIGS. 6C and 6D).

between days 3 and 8 (FIG. 5B). In contrast to HRP, Lys loaded and methanol treated films did not release substantial amounts over time (FIG. 5B).

Figure 5C:
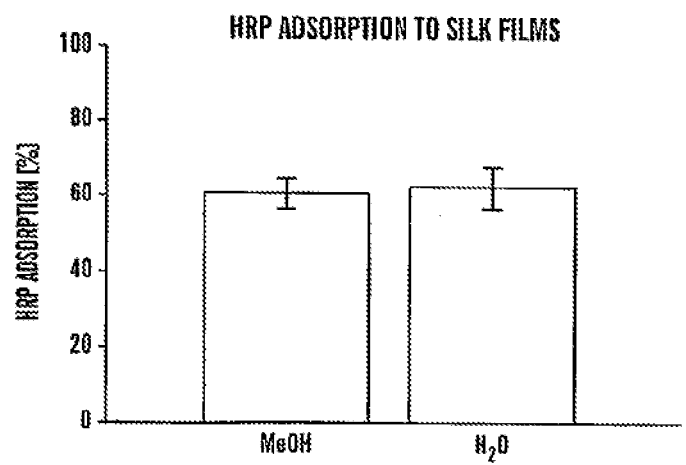
Figure 5D:
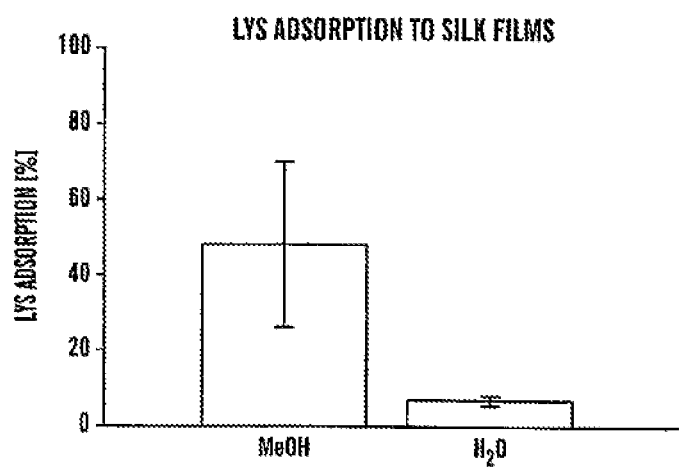

The adsorption of HRP and Lys to native film surfaces was similar for both proteins, but apparent and statistically insignificant (p=0.08) differences were observed for methanol treated films for Lys loaded films but not for HRP loaded films (FIGS. 5C and 5D).

Conclusion: Drug release from silk films was a function of the drugs molecular weight and film treatment with methanol. Sustained release profiles with a linear release of bioactive protein were observed for HRP and Lys, resulting in nearly zero order kinetics from days 3 to 8 (water treated films), whereas substantially less protein-drug activity was observed upon methanol treatment. This decrease of activity was correlated to methanol sensitivity of Lys (and to a lesser extent for HRP). Alternatively, crystallinity can be induced by water vapor treatment (data not shown) of drug loaded films at 25° C. over a saturated $Na_2SO_4$ solution for 24 hours. No loss of protein activity (Lys or HRP) is expected under these vapor conditions an assumption corroborated by preliminary findings.

TABLE 1

Groups and treatments

| I 0+ | I + 20 | I + 90 | I − 90 | II + 0 | II + 20 | II + 90 | II − 90 |
|---|---|---|---|---|---|---|---|
| FD4 preincubated with silk-fibroin solution, no MeOH treatment (n = 3) | FD4 preincubated with silk-fibroin solution, 20% MeOH treatment (n = 3) | FD4 preincubated with silk-fibroin solution, 90% MeOH treatment (n = 15) | FD4 added to silk-fibroin film, 90% MeOH treatment (n = 3) | FD4 preincubated with silk-fibroin solution, US treatment of mixture, no MeOH treatment (n = 3) | FD4 preincubated with silk-fibroin solution, US treatment of mixture, 20% MeOH treatment (n = 3) | FD4 preincubated with silk-fibroin solution, US treatment of mixture, 90% MeOH treatment (n = 9) | FD4 added to silk-fibroin film, US treatment of mixture, 90% MeOH treatment (n = 3) |

Conclusion: Methanol treatment of silk films resulted in an increase in crystallinity (β-sheet), an increase in hydrophobicity, a decrease in water solubility, and a change in surface topology.

Example 4

The release of fluorescently marked dextrans with different molecular weights was evaluated as a function of methanol treatment.

Figure 4A:
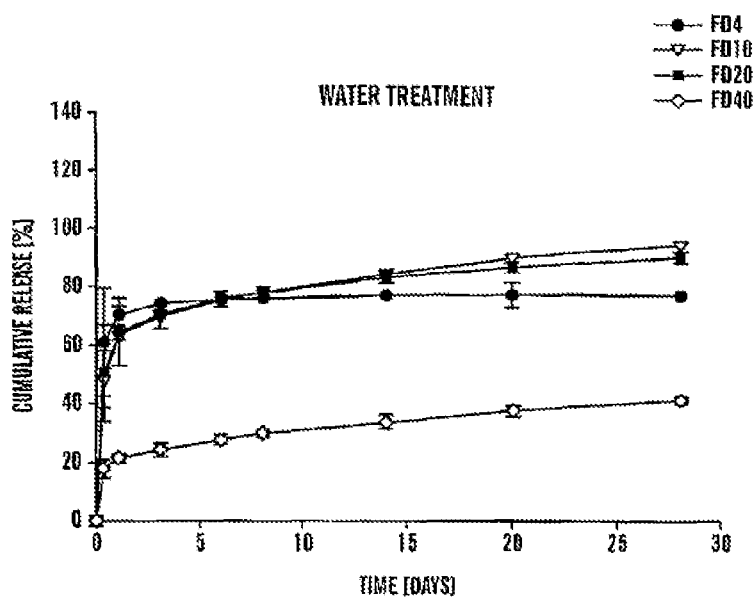
FIG. 4 shows release of FITC-dextrans with different molecular weights and from silk films treated with H2O (4A) or methanol (4B).
Figure 4B:
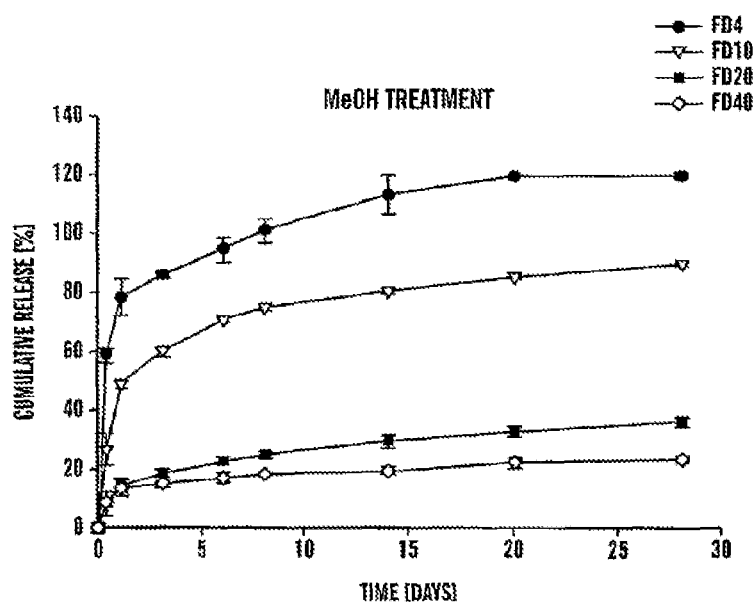

The release of dextrans with size ranges from 4 to 20 kDa was not apparently sustained, whereas the release of larger molecules (40 kDa) was retarded (FIG. 4A). In contrast, the methanol treatment of the silk films resulted in a strong retardation of release for all dextrans, particularly for molecular weights equal to or exceeding 10 kDa (FIG. 4B).

The efficacy of silk films as drug delivery systems for protein drugs was evaluated using horseradish peroxidase (HRP) and Lysozyme (Lys; FIG. 5), and analyzed by biological potency tests. A discontinuous release from native silk films was observed for HRP, characterized by an initial burst of 5% of the total loading, followed by a lag phase of two days and a continuous release from days 3 to 8 (FIG. 5A). HRP release was significantly changed after exposure of the HRP loaded films to methanol. No initial burst was observed and the HRP release started at day 5, from which on it was continuously released until day 23 (FIG. 5A). Lysozyme release from native silk films was similar to HRP, with an initial burst of about 30%, a lag phase of 1 day and a continuous release

What is claimed is:

1. A method comprising:
   a. contacting a silk fibroin solution with at least one therapeutic agent,
   b. forming a silk fibroin article comprising at least one therapeutic agent from the silk fibroin solution of (a); and
   c. altering the conformation of the silk fibroin article to provide controlled release of said at least one therapeutic agent from the silk fibroin article, wherein the alteration in conformation is induced by:
      (i) treating said silk fibroin article with shear stress;
      (ii) treating said silk fibroin article with an electric field;
      (iii) treating said silk fibroin article with pressure; or
      (iv) contacting said silk fibroin article with salt,
   and wherein the controlled release of said at least one therapeutic agent occurs over a period of about 2 to 90 days.

2. The method of claim 1, wherein the therapeutic agent is selected from the group consisting of a protein, peptide, nucleic acid, PNA, aptamer, antibody and small molecule.

3. The method of claim 1, wherein said therapeutic agent is equal to or greater than 10 kilodaltons.

4. The method of claim 1, wherein the silk fibroin solution comprises aqueous silk fibroin.

5. The method of claim 1, wherein the silk fibroin solution comprises silk fibroin in an organic solvent.

6. The method of claim 5, wherein the organic solvent is hexafluoroisopropanol (HFIP).

7. The method of claim 1, wherein the silk fibroin article is selected from the group consisting of a thread, fiber, film, foam, mesh, hydrogel, three-dimensional scaffold, tablet filling material, tablet coating, and microsphere.

8. The method of claim 1, wherein the sheer stress is applied by passing said silk fibroin article through a needle.

9. The method of claim 1, wherein said silk fibroin article comprises at least two layers, wherein at least one layer comprises an induced conformational change that differs from at least one other layer.

10. The method of claim 1, wherein said silk fibroin article is biodegradable.

11. The method of claim 1, wherein said silk fibroin article further comprises a targeting agent that specifically targets said silk fibroin article to a specific cell or tissue type.

12. The method of claim 11, wherein said targeting agent is selected from the group consisting of a sugar, peptide, and fatty acid.

13. The method of claim 1, wherein said silk fibroin solution is obtained from a solution containing a dissolved silkworm silk, spider silk or a genetically engineered silk.

14. The method of claim 13, wherein the silkworm silk is obtained from *Bombyx mori*.

15. The method of claim 13, wherein the spider silk is obtained from *Nephila clavipes*.

16. The method of claim 13, wherein said genetically engineered silk comprises a therapeutic agent.

* * * * *